US007025951B2

(12) United States Patent
Seiberg et al.

(10) Patent No.: US 7,025,951 B2
(45) Date of Patent: Apr. 11, 2006

(54) COMPOSITIONS AND METHODS FOR DARKENING THE SKIN

(75) Inventors: Miri Seiberg, Princeton, NJ (US); Connie Baozhen Lin, Belle Mead, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 214 days.

(21) Appl. No.: 10/173,755

(22) Filed: Jun. 18, 2002

(65) Prior Publication Data

US 2003/0232743 A1    Dec. 18, 2003

(51) Int. Cl.
A61K 38/00 (2006.01)
(52) U.S. Cl. .................................................. 424/59
(58) Field of Classification Search ............... 424/59
See application file for complete search history.

(56) References Cited

U.S. PATENT DOCUMENTS

| | | | |
|---|---|---|---|
| 3,755,560 | A | 8/1973 | Dickert et al. |
| 4,254,105 | A | 3/1981 | Fukuda |
| 4,421,769 | A | 12/1983 | Dixon et al. |
| 4,960,764 | A | 10/1990 | Figueroa, Jr. et al. |
| 5,216,116 | A | 6/1993 | Pawelek |
| 5,218,079 | A | 6/1993 | Pawelek et al. |
| 5,225,435 | A | 7/1993 | Pawelek et al. |
| 5,227,459 | A | 7/1993 | Pawelek et al. |
| 5,260,065 | A | 11/1993 | Mathur et al. |
| 5,384,116 | A | 1/1995 | Pawelek et al. |
| 5,618,519 | A | 4/1997 | Pawelek et al. |
| 5,744,125 | A | 4/1998 | Pawelek et al. |
| 5,763,575 | A | 6/1998 | Sundelin et al. |
| 6,245,342 | B1 | 6/2001 | Golz-Berner |

FOREIGN PATENT DOCUMENTS

| | | |
|---|---|---|
| WO | WO 98/25584 A2 | 6/1998 |
| WO | WO 96/31194 A2 | 10/1998 |
| WO | WO 99/04752 A2 | 2/1999 |
| WO | WO 99/37279 A1 | 7/1999 |
| WO | WO 00/15188 A1 | 3/2000 |
| WO | WO 00/62743 A2 | 10/2000 |

OTHER PUBLICATIONS

Michel Pruntaras, "Melanocytes, Melanogenesis and Inflammation", International Journal of Dermatology, vol 25, No. 10, Dec. 1986, pp 624-628.
PCT International Search Report Nov. 10, 2003 for corresponding PCT Application PCT/US03/19234.

John A. Wenninger, G.N. McEwen, Jr., International Cosmetic Ingredient Dictionary and Handbook, (1997), 1612-1613, 1626, 1654-1661, 1673-1686, 1693-1697 ,Seventh Edition 1997, vol. 2, The Cosmetic, Toiletry, and Fragrance Association, Washington, DC.

Miklos Bodanszky, In Search of new methods in peptide synthesis, (1985) 449-474, International J. Peptide Protein Research 25, Munksgaard International Pubbllishers Ltd. Copenhagen Denmark.

Michael Mezei, Vijeyalakshmi Gulasekharam, Liposomes-A selective drug delivery system for the topical route of administration: gel dosage form, (1982) Journal Pharm. Pharacol. 34:473-474.

Susan M. Niemiec, Chandrasekharan Ramachandran, Norman Weiner, Influence of Nonionic Liposomal Composition on Topical Delivery of Peptide Drugs Into Pilosebaceous Units: An In Vivo Study Using the Hamster Ear Model, (1995), Pharmaceutical Research, vol. 12, No. 8: 1184-1188, Plenum Publishing Corporation.

Petra Boukamp, Rule T. Petrussevska, Dirk Breitkreutz, Jurgen Hornung, Alex Markham, Norbert E. Fusenig, Normal Keratinization in a Spontaneously Immortalized Aneupiold Human Keratinocyte Cell Line, (1988). The Journal of Cell Biology, vol. 106:761-771, The Rockefeller University Press.

M. Seiberg, C. Paine, E. Sharlow, P. Andrade-Gordon, M. Costanzo, M. Eisinger, S. S. Shapiro, The Protease-Activated Receptor 2 Regulates Pigmentation via Keratinocyte-Melanocyte Interactions, (2000), Experimental Cell Research, 25-32, Academic Press.

E.R. Sharlow, C.S. Paine, L. Babiarz, M. Eisinger, S. Shapiro, M. Seiberg, The protease-activated receptor-2 upregulates keratinocyte phagocytosis (2000)Journal of Cell Science 113:3093-3101, The Company of Biologists Limited.

Miri Seiberg, Christine Paine, Elizabeth Sharlow, Patricia Andrade-Gordon, Michael Constanzo, Magdelena Eisinger and Stanley S. Shapiro, Inhibition of Melanosome Transfer Results in Skin Lightening, (2000), The Journal of Investigative Dermatology, vol. 115, No.2:162-167, The Society of Investigative Dermatology, Inc.

(Continued)

Primary Examiner—Christopher R. Tate
Assistant Examiner—Maury Audet
(74) Attorney, Agent, or Firm—William E. McGowan

(57) ABSTRACT

The present invention relates to a method of darkening the skin by topically applying to the skin a peptide and compositions containing such peptides.

28 Claims, No Drawings

OTHER PUBLICATIONS

Dezna C. Sheehan, Barbara B. Hrapchak, Theory and practice of Histotechnology, (1980), 223,224,277 Second Edition, Battle Press.

D.D. Breimer, P. Speiser, Liposomes as a Skin Drug Delivery System, Topics in Pharmaceutical Sciences (1985), Elsevier Science Publishers, New York, pp. 345-358.

McCutcheon's Emulsifiers & Detergents, 1986 North American Edition, pp. 317-324.

Cosmetics Science and Technology, 1972 John Wiley & Sons, Inc. Canada, pp. 32-43, 72-73, 443-465.

V. Santagada, G. Caliendo, B. Severino, E. Perissutti, F. Fiorino, C. Cicala, V. Defilippis, G. Cirino, Minimal Structural Requirements for Agonist Activity of PAR-2 Activating Peptides, Bioorganic & medicinal Chemistry Letters 12, (2002), 21-24. Elsevier Science Ltd.

Johnson & Johnson Consumer Companies, Inc. pending U.S. Appl. No. 09/862,145.

Johnson & Johnson Consumer Companies, Inc. pending U.S. Appl. No. 09/861,972.

Johnson & Johnson Consumer Companies, Inc. pending U.S. Appl. No. 09/861,973.

Johnson & Johnson Consumer Companies, Inc. pending U.S. Appl. No. 60/368,298.

COMPOSITIONS AND METHODS FOR DARKENING THE SKIN

FIELD OF THE INVENTION

The present invention relates to compositions and methods for darkening the skin.

BACKGROUND OF THE INVENTION

The darkening of skin color is a concern for many individuals. Most people obtain darker skin through exposure to UV light (e.g., suntanning or UV lamps). UV exposure, however, results in accelerated skin aging and increased incidence of skin cancer. The ability to generate a tanned appearance without incurring photodamage, thus, is important to many individuals. Accordingly, alternative methods for "sunless tanning" have evolved.

One method is the use of products containing dihydroxy acetone (DHA). Some of these products, however, produce color that is too orange and unnatural to the user. Moreover, the DHA-produced skin color only minimally protects the user from UV irradiation. Products containing betacarotene and cantaxanthin have also been used to darken the skin. These products, however, also result in unnatural skin color and reduced sun-protection as compared to naturally tanned skin. Thus, a product is desired that could enhance the body's natural pigment content, resulting in a desired skin color and enhanced photo-protection, without the need of UV exposure.

SUMMARY OF THE INVENTION

In one aspect, the present invention features a method of darkening the skin by topically applying to the skin a peptide of Formula I (defined below).

In another aspect, the present invention relates to a method of darkening the skin including topically applying to the skin a composition containing: a peptide of Formula I; a pigment; and a cosmetically-acceptable topical carrier.

In another aspect, the present invention features a composition containing a peptide of formula I; a pigment; and a cosmetically-acceptable topical carrier.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

Definitions

What is meant by "darkening the skin" is darkening the appearance of the skin, including, but not limited to, tanning the skin.

As used herein, "topical applying" means directly laying on or spreading on outer skin using, e.g., by use of the hands or an applicator such as a wipe, roller, or spray.

As used herein, "cosmetically-acceptable" means that the carrier, peptides, pigments, or inert ingredients which the term describes are suitable for use in contact with tissues (e.g., the skin) without undue toxicity, incompatibility, instability, irritation, allergic response, and the like. This term is not intended to limit the ingredient/product to which it describes for use solely as a cosmetic (e.g., the ingredient/product can be used as a pharmaceutical).

As used herein, "safe and effective amount" means an amount of the peptide or composition sufficient to induce a darkening of the skin, but low enough to avoid serious side effects. The safe and effective amount of the compound or composition will vary with the area being treated, the age and skin type of the end user, the duration and nature of the treatment, the specific compound or composition employed, the particular cosmetically-acceptable carrier utilized, and like factors.

Pigment

What is meant by a "pigment" is a compound(s) that can be taken up by epidermal cells in the presence of the peptides described below, resulting in visually darker look to the skin. Examples of such pigments include, but not limiting to, melanin and melanin derivatives (e.g, both melanin polymers and lower molecular weight water-soluble melanin derivatives); extracts from natural sources containing pigments such as plants (e.g., brown pigments from plants from the Hedychium genus or Bearberry genus or yellow, orange and red pigments from plants containing carotenoids or canthaxanthins); or synthetic chemicals such as compounds containing copper (e.g., copper salts such as $CuCl_2$) or synthetic carotenoids or canthaxantins. What is meant by an "extract" is a mixture of compounds isolated from a natural source (e.g., a plant). Examples of synthetic melanin derivatives are disclosed in U.S. Pat. Nos. 5,618,519, 5,384,116, and 5,227,459. Examples of soluble melanin derivatives are disclosed in U.S. Pat. Nos. 5,744,125, 5,225,435, 5,218,079, and 5,216,116. Examples of commercially available soluble melanin derivatives include Melasyn-100™ from San-mar laboratories, Inc. (Elmsford, N.Y.) and MelanZe™ from Zylepsis (Ashford, Kent, United Kingdom).

The amount of pigment present in the composition will depend on the type of pigment used. The pigment typically will be present in the composition in an amount from about 0.0001% to about 20% by weight, in particular in an amount from about 0.001% to about 5% by weight such as from about 0.01% to about 1% by weight.

Peptides

The methods and compositions of the present invention include a peptide of Formula I:

Formula I

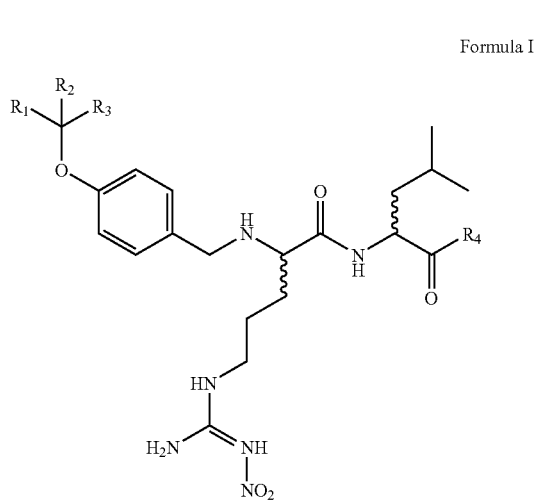

wherein $R_1$, $R_2$, and $R_3$, independently, are selected from the group consisting or H, Cl, or F; and $R_4$ is OH, $NH_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, or $C_{11-20}$ naphthylalkylamino;

or a cosmetically acceptable salt thereof.

In one embodiment, the compound is of Formula II

Formula II

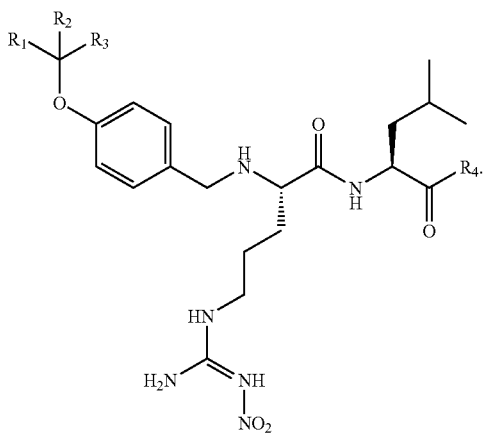

In one embodiment $R_1$, $R_2$, and $R_3$, are all either H or F.

In one embodiment $R_4$ is OH or $NH_2$.

Examples of peptides of the present invention includes, but are not limited to,

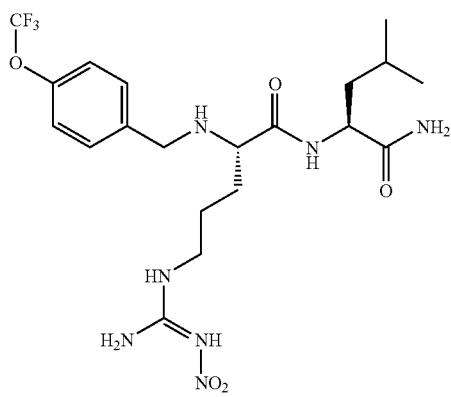

(hereinafter referred to as Peptide 1);

(hereinafter referred to as Peptide 2);

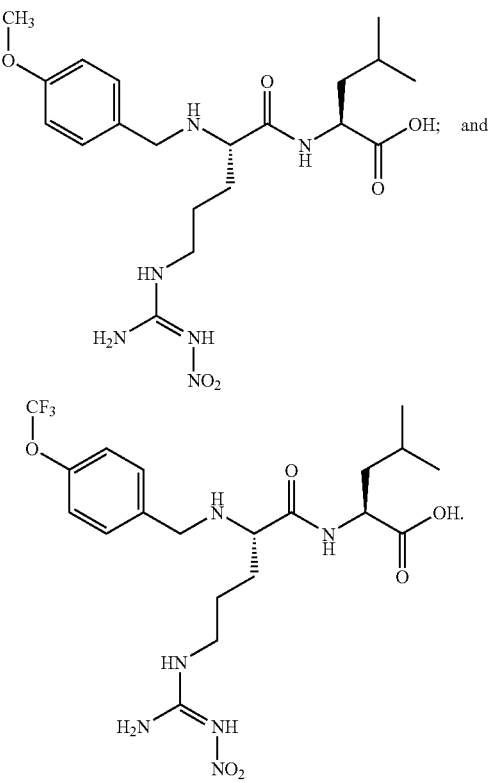

The peptide of the invention can be provided in the form of cosmetically acceptable salts. Examples of preferred salts are those with therapeutically acceptable organic acids, e.g., acetic, palmitic, oleic, stearic, lactic, maleic, citric, malic, ascorbic, succinic, benzoic, salicylic, methanesulfonic, or pamoic acid, as well as polymeric acids such as tannic acid or carboxymethyl cellulose, and salts with inorganic acids such as the hydrohalic acids (e.g., hydrochloric acid), sulfuric acid or phosphoric acid.

The amount of peptide present in the composition will depend on the peptide used. The peptide typically will be present in the composition in an amount from about 0.001% to about 10% by weight, in particular in an amount from about 0.005% to about 5% by weight such as from about 0.01% to about 1% by weight.

The method for synthesizing peptides of the present invention are well documented and are within the ability of a person of ordinary skill in the art. See, e.g., Bodanszky M, Int J Pept Protein Res 25(5):449–74 (1985) and Santagada et al., Bioorganic & Medicinal Chemistry Letters 12:21–24 (2002).

Topical Compositions

The topical compositions useful in the present invention involve formulations suitable for topical application to skin. In one embodiment, the composition comprises the peptide, pigment, and a cosmetically-acceptable topical carrier. In one embodiment, the cosmetically-acceptable topical carrier is from about 50% to abut 99.99%, by weight, of the composition (e.g., from about 80% to about 95%, by weight, of the composition.

The compositions may be made into a wide variety of product types that include but are not limited to lotions, creams, gels, sticks, sprays, ointments, cleansing liquid washes and solid bars, shampoos, pastes, foams, powders, mousses, shaving creams, wipes, patches, nail lacquers, wound dressing and adhesive bandages, hydrogels, films and make-up such as foundations, mascaras, and lipsticks. These product types may comprise several types of cosmetically-acceptable topical carriers including, but not limited to solutions, emulsions (e.g., microemulsions and nanoemulsions), gels, solids and liposomes. The following are non-limitative examples of such carriers. Other carriers can be formulated by those of ordinary skill in the art.

The topical compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, and mixtures thereof.

Topical compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32–43 (1972) and the International Cosmetic Ingredient Dictionary and Handbook, eds. Wenninger and McEwen, pp. 1656–61, 1626, and 1654–55 (The Cosmetic, Toiletry, and Fragrance Assoc., Washington, D.C., 7$^{th}$ Edition, 1997) (hereinafter "ICI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72–73 (1972) and the ICI Handbook pp. 1693–1697.

The topical compositions useful in the present invention formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, U.S. Pat. Nos. 3,755,560, 4,421,769, McCutcheon's Detergents and Emulsifiers, North American Edition, pp. 317–324 (1986), and the ICI Handbook, pp. 1673–1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. Nos. 4,254,105 and 4,960,764, are also useful in the subject invention. In general, such single or multiphase emulsions contain water, emollients, and emulsifiers as essential ingredients.

The topical compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

The topical compositions of the present invention can also be formulated into a solid formulation (e.g., a wax-based stick, soap bar composition, powder, or a wipe containing powder).

Liposomal formulations are also useful compositions of the subject invention. In one embodiment, the peptide and/or the pigment are contained within the liposome. Examples of liposomes are unilamellar, multilamellar, and paucilamellar liposomes, which may or may not contain phospholipids. Such compositions can be prepared by first combining hesperetin with a phospholipid, such as dipalmitoylphosphatidyl choline, cholesterol and water according to the method described in Mezei & Gulasekharam, "Liposomes—A Selective Drug Delivery System for the Topical Route of Administration; Gel Dosage Form", Journal of Pharmaceutics and Pharmacology, Vol. 34 (1982), pp. 473–474, or a modification thereof. Epidermal lipids of suitable composition for forming liposomes may be substituted for the phospholipid. The liposome preparation may then incorporated into one of the above carriers (e.g., a gel or an oil-in-water emulsion) in order to produce the liposomal formulation. Other compositions and uses of topically applied liposomes are described in Mezei, M., "Liposomes as a Skin Drug Delivery System", Topics in Pharmaceutical Sciences (D. Breimer and P. Speiser, eds.), Elsevier Science Publishers B. V., New York, N.Y., 1985, pp. 345–358, PCT patent application No. WO96/31194, Niemiec, et al., 12 Pharm. Res. 1184–88 (1995), and U.S. Pat. No. 5,260,065.

In one-embodiment, the liposome is non-ionic. In one example, the liposome contains (a) glycerol dilaurate; (b) compounds having the steroid backbone found in cholesterol; and (c) fatty acid ethers having from about 12 to about 18 carbon atoms. In a further embodiment, the liposome comprises glycerol dilaurate, cholesterol, polyoxyethylene-10-stearyl ether, and polyoxyethylene-9-lauryl ether. In one embodiment, these ingredients are in a ratio of about 38:12:33:17.

In one embodiment, the liposomes are present in the topical composition in an amount, based upon the total volume of the composition, of from about 10 mg/ml to about 100 mg/ml such as from about 15 mg/ml to about 50 mg/ml.

The topical compositions useful in the subject invention may contain, in addition to the aforementioned components, a wide variety of additional oil-soluble materials and/or water-soluble materials conventionally used in compositions for use on skin, hair, and nails at their art-established levels.

Additional Cosmetically Active Agents

In one embodiment, the topical composition further comprises another cosmetically active agent in addition to the peptides and pigments. What is meant by a "cosmetically active agent" is a compound (e.g., a synthetic compound or a compound isolated from a natural source) that has a cosmetic or therapeutic effect on the skin, hair, or nails, including, but not limiting to, lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removing agents and hair growing agents, firming agents, anti-callous agents, and agents for hair, nail, and/or skin conditioning.

In one embodiment, the agent is selected from, but not limited to, the group consisting of hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides such as those disclosed in PCT patent application WO00/15188 and U.S. patent application Ser. Nos. 09/861,973, 09/862,145, and 09/861,972, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera and legumes such as soy beans, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited, to glycolic acid, lactic acid, malic acid, salicylic acid, citric acid, and tartaric acid. See, e.g., European Patent Application No. 273,202.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612–13 of the ICI Handbook.

Other Materials

Various other materials may also be present in the compositions useful in the subject invention. These include humectants, proteins and polypeptides, preservatives and an alkaline agent. Examples of such agents are disclosed in the ICI Handbook, pp. 1650–1667. The compositions of the present invention may also comprise chelating agents (e.g., EDTA) and preservatives (e.g., parabens). Examples of suitable preservatives and chelating agents are listed in pp. 1626 and 1654–55 of the ICI Handbook. In addition, the topical compositions useful herein can contain conventional cosmetic adjuvants, such as dyes, opacifiers (e.g., titanium dioxide), pigments, and fragrances.

Mineral Water

The compositions of the present invention may be prepared using a mineral water, for example mineral water that has been naturally mineralized such as Evian® Mineral Water (Evian, France). In one embodiment, the mineral water has a mineralization of at least about 200 mg/L (e.g., from about 300 mg/L to about 1000 mg/L). In one embodiment, the mineral water comprises at least about 10 mg/L of calcium and/or at least about 5 mg/L of magnesium.

Legume Products

The compositions of the present invention may contain a legume product. What is meant by a "legume product" is a substance derived from a legume fruit. A legume is a plant from the family Leguminosae, which has a dehiscent fruit such as a bean, pea, or lentil. Examples of legumes, include but are not limited to, beans such as soybeans, lentil beans, peas, and peanuts. The compositions of the present invention comprise a safe and effective amount of the legume product (e.g., soy product). In one embodiment, the composition contains from about 0.001% to about 50%, from about 1% to about 30%, of the legume product (e.g., soy product).

In one embodiment, the legume product is from soy. In one embodiment, the soy product is soybean powder. Soybean powder may be made by grinding dry soybeans. In one embodiment, the soybean powder has a average particle size of less than about 10 micrometers such as less than about 1 micrometer. In one embodiment, the soybean powder has a moisture content of less than about 10% such as less than about 5%. In one embodiment, the soybean powder is lyophilized.

In one embodiment, the soy product is soymilk or soymilk powder. Soymilk is a combination of solids derived from soybeans and water, the mixture of which has some or all of the insoluble constituents filtered off. Soymilk powder is evaporated soymilk, which in one embodiment, is in a lyophilized or spray-dried form. Procedures for manufacturing soymilk include, but are not limited to, the following three procedures. First, soymilk may be made by placing soybeans into water to allow them to absorb the water. The swelled beans are then ground and additional water is then added. The mixture may then filtered to remove any insoluble residue. Second, soymilk may also be prepared from soybean powder. Soybean powder is thoroughly mixed with water (e.g., for at least one hour), which may then be followed by a filtration process to remove insoluble residues. Third, soymilk can also be reconstituted from soymilk powder by adding water. In one embodiment, soymilk comprises from between about 1% to about 50%, by weight (e.g., from about 5% to about 20%, by weight) of solids from the soybean.

EXAMPLE 1

Darkening in Pigmented Epidermal Equivalents

Peptide 1 and Peptide 2 were tested for their ability to induce darkening in pigmented epidermal equivalents. The pigmented epidermal equivalents contain human normal melanocytes, together with normal, human-derived epidermal keratinocytes, which have been cultured to form a multi-layered, highly differentiated model of the human epidermis. Type IV pigmented epidermal equivalents (consists of normal human keratinocytes pooled from variety of phototype skins and normal human melanocytes derived from type IV phototype skin) were treated with test compounds for three or five days and samples were harvested on the fourth or sixth day of the study. The harvested equivalents were stained with DOPA (a substrate for tyrosinase) or with Fontana-Mason (F&M) (Sheenan D C, Hrapckak B B, eds: Theory and practice of Histo-Thchnology (St Louis: C V Mosby, 1980) pp 223–277). F&M staining identifies silver nitrate reducing activity, which, in skin, identifies melanin.

The Epidermal equivalents used were SkinEthic® reconstructed human epidermis from SkinEthic™ Laboratory (Nice, France). UV irradiation was performed with a UVB FS light source in an exposure chamber, with plate covers removed and Phosphate—buffered saline (PBS, from Gibco-BRL, Gaithersburg, Md.) present in the lower chamber. UVB intensity was measured with a UVX radiometer (UVP Inc., San Gabriel, Calif.). Equivalents were treated with 0.1–0.12 J/cm2. No loss of viability was observed in equivalents treated with up to 0.3 J/cm2. The peptides were assayed at 100 µM, and were dissolved in PBS.

On the fourth or sixth day of the study, the equivalents were fixed, sectioned and F&M stained, or they were DOPA stained as whole without sectioning, using standard techniques. Images of stained whole or sectioned equivalents were obtained and analyzed with Image Pro Plus 3.0 software (Media Cybernetics, Silver Spring, Md.). Parameters measured were surface area of stained material within melanocyte and keratinocyte and the total surface area of the cells in culture. In all experiments there was no difference between PBS-treated cells and untreated controls. At least three sections per equivalent, three equivalents per experiment were processed. DOPA-stained epidermal equivalents were evaluated for the change in tyrosinase activity. F&M-stained histological sections were evaluated for the change in pigment deposition. Due to the low content of melanin within the equivalent, it was not possible to quantify the level of pigment within melanocytes in F&M stained sections by image analysis. Therefore, we evaluate the pigment change using the scale defined in Table 1.

TABLE 1

| Score | Description |
| --- | --- |
| 0 | No change in DOPA staining and in melanin deposition |

TABLE 1-continued

| Score | Description |
|---|---|
| 1 | Minimal increase in DOPA staining and/ or in pigment deposition |
| 2 | Increased DOPA staining and/ or in pigment deposition |
| 3 | Strong increase in DOPA staining and/ or in pigment deposition |

Table 2 represents the overall score in change of pigmentation, as evaluated by DOPA and F&M staining, as set forth above, when equivalents ere exposed Peptide 1, Peptide 2, or UVB irradiation (0.10 J/cm$^2$). These results demonstrate that Peptide 1 treatment resulted in darkening levels similar to those produced by UVB irradiation. Peptide 2 was also able to enhance pigment production.

TABLE 2

| Test Material | Score | |
|---|---|---|
| | DOPA staining (tyrosinase activity) | F & M staining (Pigment deposition) |
| Control | 0 | 0 |
| UVB (positive control) | 3 | 2 |
| Peptide 1 | 3 | 1–2 |
| Peptide 2 | 1–2 | 1–2 |

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of darkening the skin, said method comprising topically applying to the skin a peptide of the formula

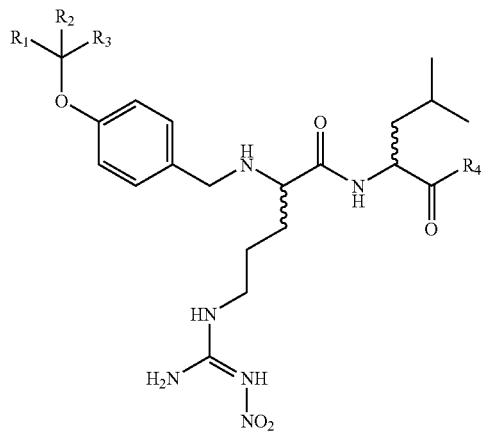

wherein $R_1$, $R_2$, and $R_3$, independently, are selected from the group consisting or H, Cl, or F; and
$R_4$ is OH, NH$_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, or $C_{11-20}$ naphthylalkylamino;
or a cosmetically acceptable salt thereof.

2. A method of claim 1, wherein said peptide is of the formula

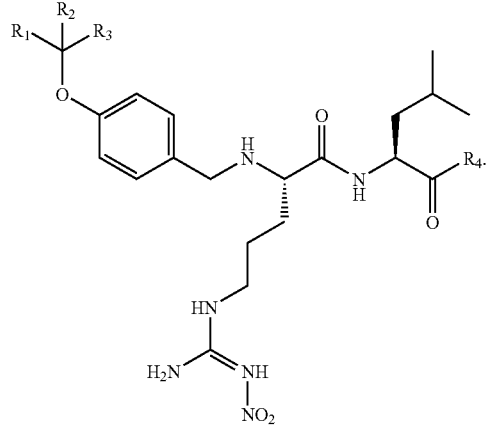

3. A method of claim 1, wherein $R_1$, $R_2$, and $R_3$ are all H and $R_4$ is OH or NH$_2$.

4. A method of claim 2, wherein $R_1$, $R_2$, and $R_3$ are all H and $R_4$ is OH or NH$_2$.

5. A method of darkening the skin, said method comprising topically applying to the skin a composition comprising:
   (a) a peptide of the formula

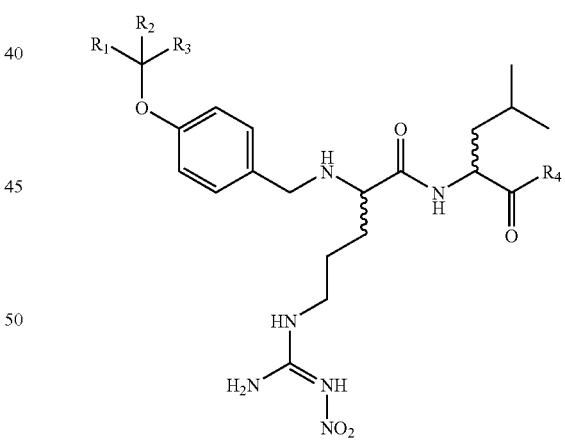

wherein $R_1$, $R_2$, and $R_3$, independently, are selected from the group consisting or H, Cl, or F; and $R_4$ is OH, NH$_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, or $C_{11-20}$ naphthylalkylamino; or a cosmetically acceptable salt thereof; and
   (b) a cosmetically-acceptable carrier.

6. A method of claim 5, wherein said peptide is of the formula

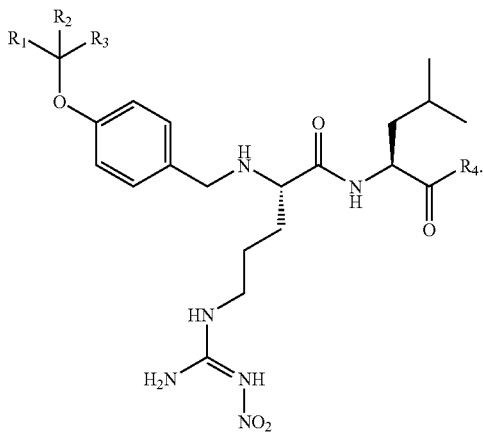

7. A method of claim 5, wherein $R_1$, $R_2$, and $R_3$ are all H and $R_4$ is OH or $NH_2$.

8. A method of claim 6, wherein $R_1$, $R_2$, and $R_3$ are all H and $R_4$ is OH or $NH_2$.

9. A method of claim 5, wherein said composition further comprises a pigment selected from the group consisting of melanin, a derivative of melanin, or a plant extract, wherein said derivative of melanin is a polymer comprising monomeric units selected from the group consisting of dihydroxyindole-carboxylic acids, 3-aminotyrosine, 3,4-dihydroxybenzoic acid, 3- amino,4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol and p-aminobenzoic acid and said plant extract is an extract from a plant of the hedychium genus or bearberry genus.

10. A method of claim 8, wherein said composition further comprises a pigment selected from the group consisting of melanin, a derivative of melanin, or a plant extract, wherein said derivative of melanin is a polymer comprising monomeric units selected from the group consisting of dihydroxyindole-carboxylic acids, 3-aminotyrosine, 3,4-dihydroxybenzoic acid, 3- amino,4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol and p-aminobenzoic acid and said plant extract is an extract from a plant of the hedychium genus or bearberry genus.

11. A method of claim 5, wherein said composition comprises from about 0.001 to about 1 percent, by weight, of said peptide.

12. A method of claim 8, wherein said composition comprises from about 0.001 to about 1 percent, by weight, of said peptide.

13. A method of claim 9, wherein said composition comprises from about 0.001 to about 1 percent, by weight, of said peptide and from about 0.0001 to about 1 percent, by weight, of said pigment.

14. A method of claim 10, wherein said composition comprises from about 0.001 to about 1 percent, by weight, of said peptide and from about 0.000 1 to about 1 percent, by weight, of said pigment.

15. A composition comprising:
(a) a peptide of the formula

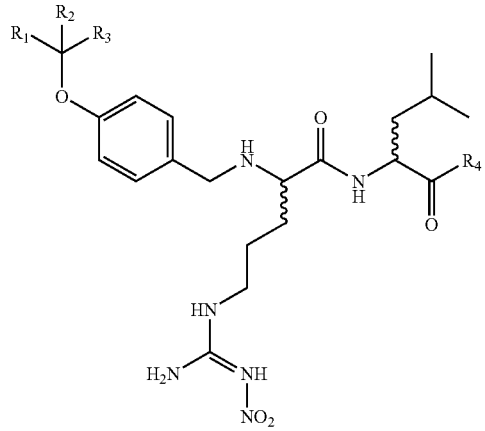

wherein $R_1$, $R_2$, and $R_3$, independently, are selected from the group consisting or H, Cl, or F; and $R_4$ is OH, $NH_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, or $C_{11-20}$ naphthylalkylamino; or a cosmetically acceptable salt thereof; and
(b) a cosmetically-acceptable carrier.

16. A composition of claim 15, wherein said peptide is of the formula

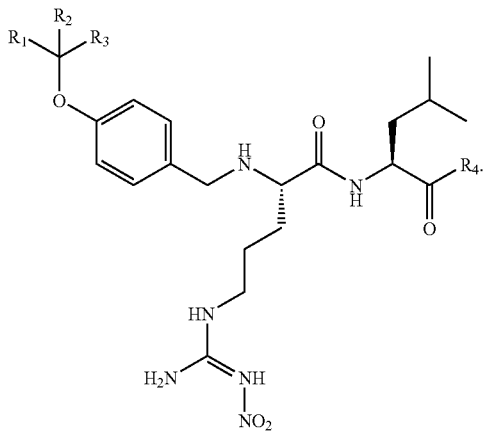

17. A composition of claim 15, wherein $R_1$, $R_2$, and $R_3$ are all H and $R_4$ is OH or $NH_2$.

18. A composition of claim 16, wherein $R_1$, $R_2$, and $R_3$ are all H and $R_4$ is OH or $NH_2$.

19. A composition of claim 15, wherein said composition further comprises a pigment selected from the group consisting of melanin, a derivative of melanin, or a plant extract, wherein said derivative of melanin is a polymer comprising monomeric units selected from the group consisting of dihydroxyindole-carboxylic acids, 3-aminotyrosine, 3,4-dihydroxybenzoic acid, 3- amino,4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol and p-aminobenzoic acid and said plant extract is an extract from a plant of the hedychium genus or bearberry genus.

20. A composition of claim 18, wherein said composition further comprises a pigment selected from the group consisting of melanin, a derivative of melanin, or a plant extract, wherein said derivative of melanin is a polymer comprising monomeric units selected from the group consisting of dihydroxyindole-carboxylic acids, 3-aminotyrosine, 3,4-dihydroxybenzoic acid, 3- amino,4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol and p-aminobenzoic acid and said plant extract is an extract from a plant of the hedychium genus or bearberry genus.

21. A composition of claim 15, wherein said composition comprises from about 0.001 to about 1 percent, by weight, of said peptide.

22. A composition of claim 18, wherein said composition comprises from about 0.001 to about 1 percent, by weight, of said peptide.

23. A composition of claim 19, wherein said composition comprises from about 0.001 to about 1 percent, by weight, of said peptide and from about 0.0001 to about 1 percent, by weight, of said pigment.

24. A composition of claim 20, wherein said composition comprises from about 0.001 to about 1 percent, by weight, of said peptide and from about 0.0001 to about 1 percent, by weight, of said pigment.

25. A method of claim 9, wherein said pigment is melanin or a derivative of melanin, wherein said derivative of melanin is a polymer comprising monomeric units selected from the group consisting of dihydroxyindole-carboxylic acids, 3-aminotyrosine, 3,4-dihydroxybenzoic acid, 3-amino,4-hydroxybenzoic acid, aloin, emodin, alizarin, tyrosine, dihydroxyphenylalanine, 4,5-dihydroxynaphthalene-2-sulfonic acid, 3- nitrotyrosine, 3-dimethylamino phenol and p-aminobenzoic acid.

26. A composition of claim 9, wherein said pigment is melanin or a derivative of melanin, wherein said derivative of melanin is a polymer comprising monomeric units selected from the group consisting of dihydroxyindole-carboxylic acids, 3-aminotyrosine, 3,4-dihydroxybenzoic acid, 3- amino,4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol and p-aminobenzoic acid.

27. A method of claim 9, wherein said pigment is a plant extract from a plant of the hedychium genus or bearberry genus.

28. A composition of claim 9, wherein said pigment is a plant extract from a plant of the hedychium genus or bearberry genus.

* * * * *